(12) United States Patent
Georges et al.

(10) Patent No.: US 9,808,416 B2
(45) Date of Patent: Nov. 7, 2017

(54) ORAL CARE COMPOSITIONS AND METHODS

(71) Applicant: Colgate-Palmolive Company, New York, NY (US)

(72) Inventors: Marian Georges, East Brunswick, NJ (US); Andre Michelle Morgan, Robbinsville, NJ (US); Sarita Vera Mello, North Brunswick, NJ (US); Pierre Lambert, Bottmingen (CH); Claude Blanvalet, Angleur (BE)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/964,175

(22) Filed: Dec. 9, 2015

(65) Prior Publication Data

US 2017/0165192 A1 Jun. 15, 2017

(51) Int. Cl.
| | | |
|---|---|---|
| *A61Q 11/00* | (2006.01) |
| *A61K 47/38* | (2006.01) |
| *A61K 6/00* | (2006.01) |
| *A61K 8/92* | (2006.01) |
| *A61K 8/21* | (2006.01) |
| *A61K 8/81* | (2006.01) |
| *A61K 8/37* | (2006.01) |
| *A61K 8/25* | (2006.01) |
| *A61K 8/73* | (2006.01) |
| *A61K 8/34* | (2006.01) |

(52) U.S. Cl.
CPC ............ *A61K 8/922* (2013.01); *A61K 8/21* (2013.01); *A61K 8/25* (2013.01); *A61K 8/34* (2013.01); *A61K 8/37* (2013.01); *A61K 8/731* (2013.01); *A61K 8/8147* (2013.01); *A61Q 11/00* (2013.01); *A61K 2800/30* (2013.01); *A61K 2800/592* (2013.01)

(58) Field of Classification Search
CPC ... A61K 2300/00; A61K 9/2054; A61Q 11/00
See application file for complete search history.

(56) References Cited

U.S. PATENT DOCUMENTS

| | | | |
|---|---|---|---|
| 5,139,768 A | 8/1992 | Friedman | |
| 5,403,577 A | 4/1995 | Friedman | |
| 5,442,001 A | 8/1995 | Jones et al. | |
| 5,849,266 A | 12/1998 | Friedman | |
| 5,976,507 A | 11/1999 | Wong et al. | |
| 8,273,405 B2 | 9/2012 | Feldstein et al. | |
| 8,444,758 B2 | 5/2013 | Stockl et al. | |
| 8,506,698 B2 | 8/2013 | Blanvalet et al. | |
| 2001/0024657 A1* | 9/2001 | Lerner et al. ......... | A61K 9/006 424/448 |
| 2008/0226567 A1* | 9/2008 | Sagel et al. .......... | A61K 8/0208 424/53 |
| 2008/0299520 A1 | 12/2008 | Ali et al. | |
| 2009/0191279 A1* | 7/2009 | Kennard et al. ........ | A61K 8/21 424/606 |
| 2009/0238777 A1 | 9/2009 | Joziak et al. | |
| 2011/0027328 A1* | 2/2011 | Baig et al. ............. | A61K 8/345 424/401 |
| 2011/0097368 A1* | 4/2011 | Jensen .................... | A61K 8/21 424/401 |
| 2013/0018069 A1* | 1/2013 | Friedman et al. ..... | A61K 9/006 514/291 |
| 2014/0242001 A1 | 8/2014 | Pillai et al. | |
| 2014/0248222 A1* | 9/2014 | Huo et al. ............ | A61K 6/0017 424/52 |
| 2015/0257983 A1* | 9/2015 | Lendenmann et al. .................... | A61K 6/0017 424/78.02 |
| 2016/0303007 A1 | 10/2016 | Blanvalet et al. | |

FOREIGN PATENT DOCUMENTS

| | | | | |
|---|---|---|---|---|
| IL | EP 0381445 B1 * | 5/1994 | .......... | A61K 6/0017 |
| WO | WO 2013/070184 | 5/2013 | | |
| WO | WO 2015/076777 | 5/2015 | | |

OTHER PUBLICATIONS

Evonik Industries. Eudragit E 100, Eudragit E PO and Eudragit E 12,5. Jul. 2015. pp. 1-6. <http://www.higuchi-inc.co.jp/pharma/excipient/eudragit/pdf/detail_eudragitE100.pdf>.*

International Search Report and Written Opinion of the International Searching Authority in International Application No. PCT/US2016/065299, dated Mar. 9, 2017.

* cited by examiner

*Primary Examiner* — Frederick Krass
*Assistant Examiner* — Tracy Liu

(57) ABSTRACT

An oral care composition and methods for making and using same are provided. In at least one embodiment, the oral care composition can include ethylcellulose, a binder, a plasticizer, a fluoride compound, a solvent, and fumed silica. In another embodiment, the oral care composition can include ethylcellulose, hydrogenated rosin, and acetyl tributyl citrate.

14 Claims, No Drawings

ORAL CARE COMPOSITIONS AND METHODS

BACKGROUND

Embodiments described herein generally relate to an oral care composition that can include ethylcellulose, a binder, a plasticizer, a fluoride compound, a solvent, and fumed silica. More particularly, some such embodiments relate to an oral care composition that can include ethylcellulose, a plasticizer, hydrogenated rosin and/or a methacrylated copolymer, and methods for making and using the same.

Dental caries is a major dental disease that affects the majority of the population. In the early 20th century, investigators found that fluoride was effective at reducing the incidence of caries. Now, fluoride compositions, such as toothpastes and mouthwashes, are routinely applied to teeth. However, it is sometimes desirable to have prolonged contact of the fluoride compositions with the teeth than is provided by toothpastes and mouthwashes, or to have compositions with higher concentrations of fluoride than what is commonly found in toothpastes or mouthwashes. For example, it can be desirable to treat tooth hypersensitivity and dental caries with high levels of fluoride for prolonged periods of time.

Dental trays have been developed into which a fluoride compositions can be added and then placed in contact with the teeth. However, this method can be inconvenient because the user must retain the dental tray in their mouth during the application. The user may find it uncomfortable and, hence, limit their time of application. Tooth varnish compositions have also been developed. These compositions can be applied with a brush, and have good adhesive characteristics to maintain contact with teeth. Tooth varnishes are typically formulated with naturally derived ingredients, such as beeswax and shellac, which can cause a temporary change in the color of the teeth, such as a yellowing. This discoloration is often undesired by the user. Other drawbacks of using naturally derived ingredients is the variability of properties due to growing and harvesting conditions and the like, and their propensity to incur phase separation in the varnishes.

There is a desire, therefore, to develop an improved oral care composition that has phase stability, which can be made from ingredients with consistent properties, and will not adversely affect the color of the teeth.

BRIEF SUMMARY

An oral care composition and methods for making and using the same are provided. In at least one specific embodiment, the oral care composition can include ethylcellulose, a binder, a plasticizer, a fluoride compound, a solvent, and fumed silica.

In another specific embodiment, the oral care composition can include from about 3 wt % to about 10 wt % ethylcellulose, from about 15 wt % to about 25 wt % hydrogenated rosin, from about 0.1 wt % to about 3 wt % acetyl tributyl citrate, from about 1 wt % to about 10 wt % sodium fluoride, from about 50 wt % to about 70 wt % solvent, and from about 1 wt % to 10 wt % fumed silica.

In another specific embodiment, the oral care composition can include from about 3 wt % to about 10 wt % ethylcellulose, from about 10 wt % to about 25 wt % of a mixture of hydrogenated rosin and methacrylate polymer, from about 0.1 wt % to about 3 wt % acetyl tributyl citrate, from about 1 wt % to about 10 wt % sodium fluoride, from about 50 wt % to about 70 wt % solvent, from about 1 wt % to 10 wt % fumed silica.

In at least one specific embodiment, a method of making an oral care composition can include mixing a fluoride compound, a binder, and a solvents to make an active ingredient premix; mixing ethylcellulose, a solvent, and fumed silica to make an ethylcellulose premix; and mixing the active ingredient premix, the ethylcellulose premix and a plasticizer additives to make the oral care composition.

In at least one specific embodiment, a method for inhibiting dental caries can include contacting an applicator to an oral care composition, where the oral care composition can include ethylcellulose, a binder, a plasticizer, a fluoride compound, a solvent, and fumed silica; and contacting the oral care composition to a tooth using the applicator.

DETAILED DESCRIPTION

It has surprisingly been found that an oral care composition including ethylcellulose, a binder, a plasticizer, a fluoride compound, a solvent, and fumed silica, which can be made from synthetic sources, has phase stability and imparts little color when applied to the teeth. Furthermore, it has been surprisingly discovered that the oral care composition also has good rheological and film-forming properties, and provides effective time-release of fluoride to the teeth. In addition, when applied to a tooth surface, the oral care composition dries out as a cosmetically desirable clear film.

Ethylcelluloses

Ethylcellulose is a derivative of cellulose in which some of the hydroxyl groups on the glucose monomer units have been chemically converted to ethyl ether groups. The one or more ethylcelluloses are can include, but are not limited to, those depicted in Formula I.

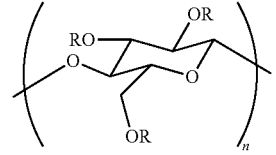

Formula I

Ethylcellulose is a large polymeric molecule composed of glucose monomer units; n in Formula I can be on the order of tens of thousands or more. The number of ethyl ether groups depends upon the synthetic conditions; R in Formula I can be H or $CH_2CH_3$.

The ethylcellulose can be used to form biostructures, such as matrices, microspheres, or microparticles, for the microencapsulation of active ingredients, such as fluoride, as a means of controlling their solubility rates. The one or more ethylcelluloses that can be used in the oral care composition can have various chemical and physical properties. For example, ethylcelluloses can have chemical and physical properties such as: bulking density in granular form of about 2.6 to about 2.8 lbs/gal, a bulking value in solution of about 0.099 to about 0.104 gal/lb, a softening point of about 152° C. to about 162° C., a specific gravity of about 1.14, a specific volume of about 23.9 in.$^3$/lb in solution, a tensile strength of about 6,800 lbs/in.$^2$ to about 10,500 lbs/in.$^2$ for a dry 3-mil film, and an ethoxyl content of about 40% to about 60% of the hydroxyl groups converted to ethyl ether groups.

Commercially available ethylcellulose can be used in the oral care composition can include, but are not limited to, those manufactured by Ashland, Inc. of Covington, Ky., such as AQUALON® N22 ethylcellulose, and those manufactured by Dow Chemical Company of Midland, Mich., such as ETHOCEL® ethylcellulose.

The total weight of the composition can include the total weight of the one or more ethylcelluloses, the one or more binders, the one or more plasticizers, the one or more fluoride compounds, the one or more solvents, the one or more fumed silica, and the one or more additives.

In an embodiment, the oral care composition can include one or more ethylcelluloses from a low of about 0.1 wt %, about 1 wt %, about 2 wt %, or about 3 wt % to a high of about 10 wt %, about 15 wt %, about 25 wt %, or about 35 wt %, based on the total weight of the composition. For example, the oral care composition can include one or more ethylcelluloses from about 0.1 wt % to about 4 wt %, about 3 wt % to about 7 wt %, about 5 wt % to about 15 wt %, about 6 wt % to about 6.75 wt %, about 9 wt % to about 16 wt %, about 10 wt % to about 20 wt %, about 12 wt % to about 26 wt %, about 15 wt % to about 30 wt %, about 21 wt % to about 32 wt %, about 17 wt % to about 27 wt %, or about 24 wt % to about 35 wt %, based on the total weight of the composition. In one embodiment, the ethylcellulose is contained in an amount of from about 3 wt % to about 10 wt %, or from about 5 wt % to about 7 wt %, or from about 6 wt % to about 6.75 wt %, based on the total weight of the composition.

Binders

The one or more binders can include one or more hydrogenated rosins, one or more methacrylate copolymers, and mixtures thereof. Hydrogenated rosins are rosin acids or resin acids, which have had some their carbon-carbon double bonds hydrogenated. This hydrogenation gives the rosins resistance to air oxidation. Rosin acids that can be hydrogenated can include, but are not limited to: abietic-type acids, such as abietic acid, dihydroabietic acid, neoabietic acid, palustric acid, and levopimaric acid, and pimaric acid, such as pimaric acid and isopimaric acid. Scheme I depicts the hydrogenation of the rosin acid, abietic acid, to dihydroabietic acid and tetrahydroabietic acid.

Scheme I

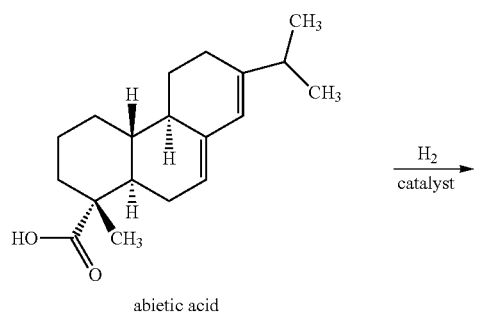

abietic acid

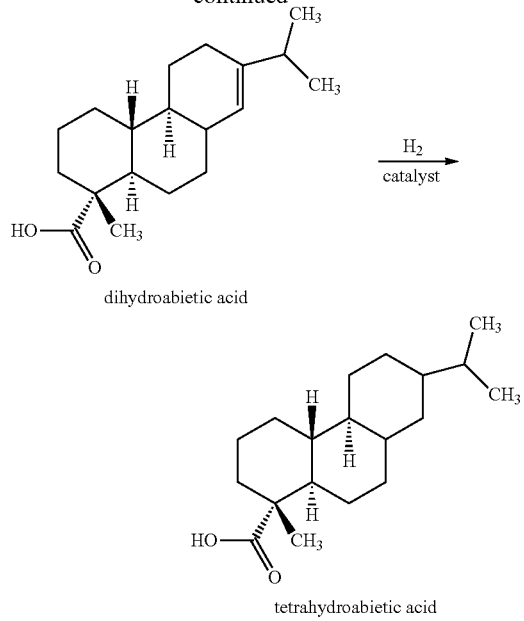

dihydroabietic acid tetrahydroabietic acid

The hydrogenated rosins that can be used in the oral care composition can have various chemical and physical properties. For example, hydrogenated rosins can have chemical and physical properties such as: a softening point of about 79° C. to about 87° C., an acid number of about 165 mg KOH/g, and a refractive index of about 1.4952 at 100° C.

Commercially available hydrogenated rosins can be used as a binder in the oral care composition disclosed herein. Such commercially available hydrogenated rosins can include, but are not limited to, FLORAL® AX-E fully hydrogenated rosin manufactured by the Eastman Chemical Company of Kingsport, Tenn.

As noted above, some embodiments, the one or more binders can include one or more methacrylate copolymers. The methacrylate copolymers can include, but are not limited to, those depicted in Formula II.

Formula II

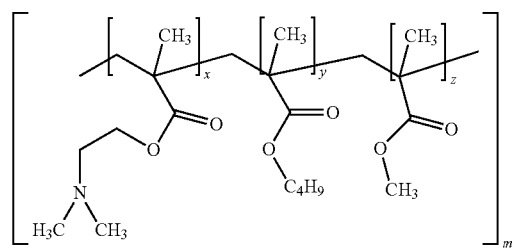

Methacrylate copolymers are large polymeric molecules composed of substituted methacrylate monomer units; m can be on the order of tens of thousands or more. In Formula II, the x monomer is dimethylaminoethyl methacrylate, the y monomer is butyl methacrylate, and the z monomer is methyl methacrylate. The ratio of x to y to z can be any ratio depending upon the desired chemical and physical properties of the methacrylate copolymers. For example, the x:y:z can be 2:1:1. The methacrylate copolymers can include, but are not limited to: butylated methacrylate copolymer, amino methacrylate copolymer, and aminoalkylmethactylate copolymer.

The methacrylate copolymers that can be used in the oral care composition can have various chemical and physical properties. For example, methacrylate copolymers can have chemical and physical properties such as: a molecular weight of about 47,000 g/mol, a refractive index of about 1.380 to about 1.385, an alkali value of about 180 mg KOH/g of copolymer, and a glass transition temperature of about 45° C.

Commercially available methacrylate copolymers can be used as the binder in the oral care composition disclosed herein. Such commercially available methacrylate copolymers can include, but are not limited to, the EUDRAGIT® family of methacrylate copolymers, such as EUDRAGIT® E 100, EUDRAGIT® E PO, and EUDRAGIT® E12,5, manufactured by Evonik Industries of Essen, North Rhine-Westphalia, Germany.

The oral care composition can include one or more binders from a low of 0.1 wt %, about 1 wt %, about 2 wt %, or about 3 wt % to a high of about 10 wt %, about 15 wt %, about 25 wt %, or about 35 wt %, based on the total weight of the composition. For example, the oral care composition can include one or more binders from about 0.01 wt % to about 0.1 wt %, about 0.1 wt % to about 1 wt %, about 1 wt % to about 5 wt %, about 3 wt % to about 9 wt %, about 7 wt % to about 15 wt %, about 10 wt % to about 15 wt %, about 10 wt % to about 20 wt %, about 12 wt % to about 25 wt %, about 14 wt % to about 28 wt %, about 19 wt % to about 20 wt %, or about 20 wt % to about 35 wt %, based on the total weight of the composition. In one embodiment, the oral care composition can include a binder in an amount of from about 10 wt % to about 25 wt %, or from about 12 wt % to about 22 wt %, based on the total weight of the composition. In one embodiment, the binder is a hydrogenated rosin and is contained in the oral care composition in an amount of from about 15 wt % to about 25 wt %, or from about 17 wt % to about 23 wt %, or from about 19 wt % to about 21 wt %, based on the total weight of the composition. In another embodiment, the binder is a methacrylate polymer and is contained in the oral care composition in an amount of from about 10 wt % to about 15 wt %, or from about 11 wt % to about 13 wt %, based on the total weight of the composition. In another embodiment, the binder is a combination of a methacrylate polymer and a hydrogenated rosin, and the binder is contained in the oral care composition in an amount of from about 10 wt % to about 25 wt %, or from about 12 wt % to about 20 wt %, or from about 12 wt % to about 17 wt %, or from about 13 wt % to about 15 wt %, based on the total weight of the composition.

Plasticizers

Plasticizers are compounds that increase the fluidity of a material. Plasticizers that can be used in the oral care composition can include, but are not limited to, citric acid esters, such as acetyl tributyl citrate and acetyl triethyl citrate.

Suitable acetyl tributyl citrate can have various chemical and physical properties such as: a molecular formula of $C_{20}H_{34}O_8$, a molecular weight of about 403.5 g/mol, a vapor pressure of about 0.8 mmHg at 170° C., a specific gravity of about 1.048, a vapor density of about 14.1, a freezing point of about −59° C., a boiling point of about 327° C., and a solubility in water of less than 0.1% at 25° C.

Commercially available acetyl tributyl citrate can be used as a plasticizer in the oral care composition disclosed herein. Such commercially available acetyl tributyl citrate can include, but is not limited to, CITROFLEX® A-4, manufactured by Vertellus Performance Materials Inc. of Greensboro, N.C.

Suitable acetyl triethyl citrate can have various chemical and physical properties such as: a molecular formula of $C_{14}H_{22}O_8$, a molecular weight of about 318.30 g/mol, a vapor pressure of about 1.00 mmHg at 170° C., a specific gravity of about 1.135, a vapor density of about 11.1, a freezing point of about −42° C., a boiling point of about 297° C., and a solubility in water of about 0.72% at 25° C.

Commercially available acetyl triethyl citrate can be used as a plasticizer in the oral care composition disclosed herein. Such commercially available acetyl triethyl citrate can include, but is not limited to, CITROFLEX® A-2, manufactured by Vertellus Performance Materials Inc. of Greensboro, N.C.

The oral care composition can include one or more plasticizers from a low of about 0.01 wt %, about 0.1 wt %, about 1.5 wt %, or about 2 wt % to a high of about 4 wt %, about 5 wt %, about 10 wt %, or about 15 wt %, based on the total weight of the composition. For example, the oral care composition can include one or more plasticizers from about 0.01 wt % to about 0.1 wt %, about 0.05 wt % to about 0.15 wt %, about 1 wt % to about 1.5 wt %, about 1 wt % to about 2 wt %, about 1.5 wt % to about 3 wt %, about 2 wt % to about 5 wt %, about 1 wt % to about 6 wt %, about 1.1 wt % to about 4.0 wt %, about 3 wt % to about 7 wt %, or about 6 wt % to about 15 wt %, based on the total weight of the composition. In one embodiment, the oral care composition can include a plasticizer in an amount of from about 0.1 wt % to about 3 wt %, or from about 0.5 wt % to about 2 wt %, or from about 1 wt % to about 1.5 wt %, based on the total weight of the composition.

Fluoride Compounds

An active ingredient for the oral composition can include one or more fluoride compounds, which provide fluoride ions when in contact with (e.g., after mixing in the mouth) the user's saliva. Fluoride compounds can include, but are not limited to: sodium fluoride, potassium fluoride, calcium fluoride, zinc fluoride, zinc ammonium fluoride, lithium fluoride, ammonium fluoride, stannous fluoride, stannous fluorozirconate, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, and amine fluorides.

The oral care composition can include one or more fluoride compounds from a low of about 0.1 wt %, about 1 wt %, about 2 wt %, or about 3 wt % to a high of about 6 wt %, about 9 wt %, about 12 wt %, or about 20 wt %, based on the total weight of the composition. For example, the oral care composition can include one or more fluoride compounds from about 0.01 wt % to about 0.1 wt %, about 0.1 wt % to about 1 wt %, about 1 wt % to about 4 wt %, about 2 wt % to about 6 wt %, about 4 wt % to about 5 wt %, about 4 wt % to about 8 wt %, about 5 wt % to about 10 wt %, about 7 wt % to about 12 wt %, about 11 wt % to about 18 wt %, about 13 wt % to about 17 wt %, or about 8 wt % to about 20 wt %, based on the total weight of the composition. In one embodiment, the oral care composition can include a fluoride compound in an amount of from about 1 wt % to about 10 wt %, or from about 3% to about 7 wt %, or from about 4 wt % to about 5 wt %, based on the total weight of the composition.

In another aspect, the fluoride compounds can dissociate to provide fluoride ions in a concentration from a low of about 5,000 ppm, about 7,000 ppm, about 9,000 ppm, or about 10,000 ppm to a high of about 20,000 ppm, about 30,000 ppm, 40,000, or about 50,000 ppm. For example, the one or more fluoride compounds can dissociate to provide fluoride ions in a concentration from about 5,000 ppm to about 7,000 ppm, about 6,000 ppm to about 12,000 ppm, about 11,000 ppm to about 21,000 ppm, about 19,000 ppm to about 27,000 ppm, about 26,000 ppm to about 37,000 ppm, about 25,000 ppm to about 37,000 ppm, about 28,000 ppm to about 50,000 ppm. In order to provide such a concentration in the desired ppm range, the exact weight percentage of the one or more fluoride compounds in the oral care composition can vary widely, depending upon the stoichiometric ratio of the fluoride within the compound.

Solvents

The solvents can include, but are not limited to: methanol, ethanol, ethyl acetate, acetone, isopropanol, and mixtures thereof. In various embodiments, the solvent in the oral care composition will evaporate, either fully or partially, when applied to the teeth of the user. The solvent can act as a viscosity modifier, aiding in the deposition of the oral care composition to form an even and consistent film on the user's teeth.

The oral care composition can include one or more solvents from a low of about 40 wt %, about 45 wt %, about 50 wt %, or about 55 wt % to a high of about 60 wt %, about 65 wt %, about 70 wt %, or about 80 wt %, based on the total weight of the composition. For example, the oral care composition can include one or more solvents from about 40 wt % to about 50 wt %, about 45 wt % to about 55 wt %, about 54 wt % to about 66 wt %, about 60 wt % to about 64.5 wt %, about 61 wt % to about 70 wt %, about 68 wt % to about 77 wt %, about 70 wt % to about 80 wt %, about 71 wt % to about 80 wt %, based on the total weight of the composition. In one embodiment, the solvent is contained in an amount of from about 50 wt % to about 70 wt %, or from about 55 wt % to about 65 wt %, or from about 58 wt % to about 62 wt %, based on the total weight of the composition.

Fumed Silica

Fumed silica or pyrogenic silica is made by heating, e.g., over a flame, amorphous, particulate silicon dioxide ($SiO_2$) to produce branched, chainlike, three-dimensional secondary particles that agglomerate into tertiary particles. The fumed silica can have a low bulk density and a high surface area. The fumed silica can increase the viscosity and the thixotropic rheology of the oral composition.

The fumed silica can have various chemical and physical properties such as: aggregate spheres with lengths from about 0.1 microns to about 0.2 microns and about 3.5 to about 4.5 hyroxyl groups per square millimicron of silica surface.

Commercially available fumed silica can be used in the oral care composition disclosed herein. Such commercially available fumed silica can include, but is not limited to, AEROSIL® fumed silica manufactured by Evonik Industries of Essen, North Rhine-Westphalia, Germany.

The oral care composition can include one or more fumed silica from a low of about 0.1 wt %, about 1 wt %, about 2 wt %, or about 3 wt % to a high of about 6 wt %, about 9 wt %, about 12 wt %, or about 20 wt %, based on the total weight of the composition. For example, the oral care composition can include fumed silica from about 0.01 wt % to about 0.1 wt %, about 0.1 wt % to about 1 wt %, about 1 wt % to about 4 wt %, about 2 wt % to about 6 wt %, about 4.5 wt % to about 5 wt %, about 4 wt % to about 8 wt %, about 5 wt % to about 10 wt %, about 7 wt % to about 12 wt %, about 11 wt % to about 18 wt %, about 13 wt % to about 17 wt %, or about 8 wt % to about 20 wt %, based on the total weight of the composition. In one embodiment, the fumed silica is contained in an amount of from about 1 wt % to about 10 wt %, or from about 2 wt % to about 8 wt %, or from about 4 wt % to about 6 wt %, based on the total weight of the composition.

Additives

The one or more additives can include, but are not limited to: one or more flavoring agents, one or more sweetening agents, one or more surfactants, one or more anti-sensitivity agents, one or more anti-microbial agents, one or more anti-caries agents, one or more anti-calculus agents, one or more acids, one or more bases, one or more tooth whitening agents, anti-inflammatory agents, one or more vitamins, one or more pigments, one or more coloring agents, one or more enzymes, one or more preservatives, and one or more tartar control agents.

The flavoring agents can include, but are not limited to: oils of spearmint, peppermint, wintergreen, sassafras, clove, sage, eucalyptus, marjoram, cinnamon, lemon, lime, grapefruit, and orange; menthol; carvone; anethole; raspberry 73562; cyclamates; acesulfane-K; thaumatin; neohisperidin dihydrochalcone; D-tryptophan, ammoniated glycyrrhizin; and mixtures thereof.

The sweetening agents can include, but are not limited to: saccharin, xylitol, perillartien, sucrose, glucose, sucralose, dextrose, levulose, lactose, thaumatin, neohisperidin dihydrochalcone, mannitol, sorbitol, fructose, maltose, xylitol, thaumatin, aspartame, dihydroehalcones, xylitol, acesulfame, cyclamate salts, and mixtures thereof.

Acids and/or bases can be used to adjust the pH and buffer the oral care composition. The acids can include, but are not limited to: sodium carbonate, sodium bicarbonate, sodium dihydrogen phosphate, sodium hydrogen phosphate, trisodium phosphate, sodium hydroxide, sodium carbonate, citric acid, sodium citrate, and mixtures thereof. The bases can include, but are not limited to: sodium hydroxide, potassium hydroxide, and mixtures thereof. The oral care composition can have a pH from a low of 4.0 to a high of about pH 9.0. For example, the oral care composition can have pH from about 4.0 to about 5.0, about 4.5 to about 6.0, about 5.5 to about 6.5, about 6.0 to about 7.0, about 6.5 to about 8.0, or about 7.5 to about 9.0.

The surfactants can be anionic, cationic, zwitterionic, nonionic surfactants, and mixtures thereof. The one or more surfactants can include, but are not limited to: alkyl sulfates, sulfonated monoglycerides, sodium lauryl sulfate, sodium lauroyl sarcosmate, sodium coconut monoglyceride sulfonates, sodium ether lauryl, and mixtures thereof.

The anti-microbial agents can include, but are not limited: benzoic acid, sodium benzoate, potassium benzoate, boric acid, betanaphthol, chlorothymol, thymol, anethole, eucalyptol, carvacrol, menthol, phenol, amylphenol, hexylphenol, heptylphenol, octylphenol, hexylresorcinol, laurylpyridinium chloride, myristylpyridinium chloride, cetlpyridinium fluoride, cetylpyridinium chloride, cetylpyridinium bromide, triclosan, and mixtures thereof.

The anti-sensitivity agents can include, but are not limited: potassium salts such as potassium nitrate, potassium bicarbonate, potassium chloride, potassium citrate, and potassium oxalate; capsaicin; eugenol; strontium salts; zinc salts; chloride salts; and mixtures thereof. The oral care composition may treat hypersensitivity by blocking dentin tubules.

The tooth whitening agents can include, but are not limited to: peroxides, such as hydroperoxides, hydrogen peroxide, lithium peroxide, potassium peroxide, sodium peroxide, magnesium peroxide, calcium peroxide, barium peroxide, peroxy acids; metal chlorites, such as calcium chlorite, barium chlorite, magnesium chlorite, lithium chlorite, sodium chlorite, and potassium chlorite; persulfates; sodium perborate; and mixtures thereof.

The oral care composition can include one or more additives from a low of about 0.1 wt %, about 1 wt % to about 1.75 wt %, about 1 wt %, about 2 wt %, or about 3 wt % to a high of about 6 wt %, about 9 wt %, about 12 wt %, or about 20 wt %, based on the total weight of the composition. For example, the oral care composition can include one or more additives from about 0.01 wt % to about 0.1 wt %, about 0.1 wt % to about 1 wt %, about 1 wt % to about 4 wt %, about 2 wt % to about 6 wt %, about 4.5 wt % to about 5 wt %, about 4 wt 0/% to about 8 wt %, about 5 wt % to about 10 wt %, about 7 wt % to about 12 wt %, about 11 wt % to about 18 wt %, about 13 wt % to about 17 wt %, or about 8 wt % to about 20 wt %, based on the total weight of the composition.

The one or more additives can include water. However, in an aspect, the oral care composition is nonaqueous or has a low concentration of water because water may dissolve and dissociate the one or more fluoride compounds. The fluoride compounds can be the active ingredient in the oral composition, and it can be more efficacious to allow the water in the user's saliva to dissolve the fluoride compounds. For the present disclosure, nonaqueous is defined as having a water concentration from a low of 0 wt %, about 0.1 wt %, about 1 wt %, or about 1.5 wt % to a high of about 2 wt %, about 3 wt %, about 4 wt %, or about 5 wt %, based on the total weight of the composition. For example, the oral care composition can include water from about 0.01 wt % to about 0.1 wt %, about 0.1 wt % to about 1 wt %, about 1 wt % to about 1.5 wt %, about 1.5 wt % to about 2 wt %, or about 1.9 wt % to about 5 wt %, based on the total weight of the composition. Water can be added directly to the oral care composition, absorbed from the ambient air, or added from the small amounts contained in the one or more hydrogenated rosins, the one or more methacrylate copolymers, the one or more ethylcelluloses, the one or more plasticizers, the one or more fluoride compounds, the one or more solvents, or the one or more additives.

The one or more additives can include beeswax and/or shellac. However, in an aspect, the oral care composition can be free of or have a low concentration of beeswax and/or shellac. For the present disclosure, free of or having a low concentration of beeswax and/or shellac is defined as having a concentration from a low of 0 wt %, about 0.1 wt %, about 1 wt %, or about 1.5 wt % to a high of about 2 wt %, about 3 wt %, about 4 wt %, or about 5 wt %, based on the total weight of the composition.

The oral care composition can be a liquid, dispersion, suspension, gel, solution, solid, or any mixture thereof. The rheological properties of the oral care composition can vary widely. The oral care composition can have viscosity from a low of about 1 centipoise ("cP"), about 100 cP, about 250 cP, about 500 cP, or about 700 cP to a high of about 1,000 cP, about 3,250 cP, about 4,500 cP, about 5,000 cP, or about 10,000 cP at a temperature of about 25° C. For example, the oral care composition can have a viscosity from about 10 cP to about 125 cP, about 20 cP to about 75 cP, about 75 cP to about 125 cP, about 260 cP to about 460 cP, about 725 cP to about 1,100 cP, about 4,100 cP to about 8,600 cP, about 8,600 cP to about 9,200 cP, or about 7,900 cP to about 9,990 cP at a temperature of about 25° C. In another example, the oral care composition can have a viscosity from about 1 cP to about 450 cP, about 450 cP to about 1,205, about 6,250 cP to about 7.550 cP, about 6,550 cP to about 8,250 cP, about 7,250 cP to about 9,100 cP, about 8,100 cP to about 9,600 cP, or about 6,600 cP to about 8,200 cP at a temperature of about 25° C. The viscosity can be measured using a viscometer.

The oral care composition can have a high-shear viscosity from a low of about 0.2 Pascal second ("Pa·s"), about 0.4 Pa·s, about 1 Pa·s, or about 1.5 Pa·s to a high of about 4 Pa·s, Pa·s, about 5 Pa·s, about 6 Pa·s, or about 7 Pa·s at a temperature of about 25° C. For example, the oral care composition can have a high-shear viscosity from about 0.2 Pa·s to about 0.5 Pa·s, about 0.5 Pa·s to about 1 Pa·s, about 0.9 Pa·s to about 2 Pa·s, about 1.5 Pa·s to about 3 Pa·s, about 2.5 Pa·s to about 3.7 Pa, about 3.25 Pa·s to about 3.45 Pa·s, about 3.4 Pa·s to about 4.5 Pa·s, about 3 Pa·s to about 5 Pa·s, about 3 Pa·s to about 5 Pa·s, or about 4.5 Pas to about 7 Pa·s, at a temperature of about 25° C.

The oral care composition can have a yield stress (up) from a low of about 100 Pa, about 120 Pa, about 140 Pa, or about 170 Pa to a high of about 275 Pa, about 320 Pa, about 375 Pa, or about 300 Pa, at a temperature of about 25° C. For example, the oral care composition can have a yield stress (up) from about 150 Pa to about 165 Pa, about 164 Pa to about 175 Pa, about 180 Pa to about 190 Pa, about 175 Pa to about 200 Pa, about 195 Pa to about 225 Pa, about 220 Pa to about 270 Pa, about 260 Pa to about 325 Pa, about 300 Pa to about 355 Pa, about 330 Pa to about 375 Pa, or about 370 Pa to about 400 Pa, at a temperature of about 25° C.

The oral care composition can have a yield stress (down) from a low of about 150 Pa, about 170 Pa, about 180 Pa, or about 190 Pa to a high of about 225 Pa, about 250 Pa, about 275 Pa, or about 300 Pa, at a temperature of about 25° C. For example, the oral care composition can have a yield stress (down) from about 150 Pa to about 175 Pa, about 180 Pa to about 190 Pa, about 165 Pa to about 200 Pa, about 190 Pa to about 220 Pa, about 195 Pa to about 235 Pa, about 210 Pa to about 245 Pa. about 230 Pa to about 265 Pa, about 260 Pa to about 300 Pa, about 330 Pa to about 375 Pa, or about 370 Pa to about 400 Pa, at a temperature of about 25° C.

The oral care composition can have a specific gravity from a low of about 0.870, about 0.880, about 0.890, or about 0.900 to a high of about 1.000, about 1.100, about 1.150, or about 1.200, at a temperature of about 25° C. For example, the oral care composition can have a specific gravity from about 0.870 to about 0.890, about 0.880 to about 0.895, about 0.890 to about 1.000, about 0.940 to about 1.100, about 1.000 to about 1.120, about 1.100 to about 1.169, or about 1.600 to about 1.200, at a temperature of about 25° C.

Further disclosed herein are methods of making the oral care composition. The oral care composition can, in certain embodiments, be prepared by adding and mixing the ingredients of the composition in a vessel, which may be provided with a mixer. In an embodiment, the ingredients can be mixed all together or in any order to form a homogenous dispersion, suspension, and/or solution. In another embodiment, a premix suspension of the active ingredient, such as the fluoride compound, can be made and a premix suspension of the ethylcellulose can be made. The premix suspension of the active ingredient and the premix suspension of the ethylcellulose can then be mixed together to form the oral care composition. For example, in a vessel a fluoride premix can be made by adding one or more fluoride compounds, one or more binders, one or more additives, one or more solvents, and mixing until a homogenous dispersion, suspension, and/or solution is formed. An ethylcellulose premix can be made in a separate vessel by adding one or more ethylcelluloses, one or more solvents, one or more fumed silica, and one or more additives, and mixing until a homogenous dispersion, suspension, and/or solution is formed. The fluoride premix, the ethylcellulose premix, and the one or more plasticizers can then be combined and mixed until a homogenous dispersion, suspension, gel, and/or solution is formed into an oral care composition.

Further disclosed herein are methods of using the oral care composition. The oral care composition can be applied to the surface of a tooth to inhibit dental caries. The oral care composition facilitates the adhesion of the active component, such as one or more fluoride compounds, to the surface of the tooth. The rheological and film-forming properties of the oral care composition allow for effective contact of the active ingredient to the tooth, forming a thin film over the dental surface. The user's saliva can then begin to dissolve the active ingredient. For example, the user's saliva can dissolve the one or fluoride compounds, releasing fluoride ions to aid in the remineralization of the tooth and neutralizing acids produced by bacteria.

The oral care composition can be applied to a tooth by any means. An applicator, such as a brush or a dental tray, can be used to apply the composition. For example, the oral care composition can be applied by contacting a brush with the composition and then using the brush to contact the composition to the surface of a tooth. Or in other words, by painting or brushing the composition onto a user's teeth. Over time the oral care composition wears off of the surface of the tooth. In various embodiments, the oral care composition may wear off about 2 hours after application, about 6 hours after application, about 12 hours after application, about 24 hours after application, or about 36 hours after application.

EXAMPLES

In order to provide a better understanding of the foregoing discussion, the following non-limiting examples are offered. Although the examples can be directed to specific embodiments, they are not to be viewed as limiting the invention in any specific respect.

Active Ingredient (Fluoride) Premix 1

An active ingredient (fluoride) premix was made by adding ethanol (50 wt %) and saccharin (0.67 wt %) to a plastic beaker and mixing until the saccharin was dissolved. FLORAL® AX-E Fully Hydrogenated Rosin (20.00 wt %) was slowly added while mixing with an overhead mixer until dissolved. Sodium fluoride (4.97 wt %) was added and mixed for 30 minutes until a homogeneous solution was formed.

Ethylcellulose Premix 1

An ethylcellulose premix was made by slowly adding AQUALON® N22 ethylcellulose (6.50 wt 0%) to ethanol (10.92 wt 0%) in a plastic beaker, and slowly mixing to avoid lumps. Once the ethylcellulose was incorporated, fumed silica (5.00 wt %) was added and mixed for 30 minutes until the solution was homogenous.

Oral Care Composition 1

The active ingredient (fluoride) premix 1 and the ethylcellulose premix 1 were mixed together in a plastic beaker. CITROFLEX® A-4 (1.30 wt %) was added and mixed for 10 minutes. Raspberry 73562 (0.64 wt 0%) was added and mixed for 15 minutes to make the oral care composition 1.

The specific gravity of the Oral Care Composition 1 was measured at 1.024. The rheology of the oral care composition 1 was measured.

TABLE 1

Example Oral Care Composition 1

| Ingredients | Weight (%) |
|---|---|
| Ethanol | 60.92 |
| Sodium Fluoride | 4.97 |
| Saccharin | 0.67 |
| Fumed Silica | 5.00 |
| Flavor agent (Raspberry 73562) | 0.64 |
| AQUALON ® N22 Ethylcellulose | 6.50 |
| CITROFLEX ® A-4 | 1.30 |
| FLORAL ® AX-E Fully Hydrogenated Rosin | 20.00 |
| Totals | 100.00 |
| Specific Gravity | 1.024 |

Table 2 lists Comparative Example 1 made from natural ingredients beeswax and shellac.

TABLE 2

Comparative Example I

| Ingredients | Weight % |
|---|---|
| 96% Ethanol | 27.21 |
| Sodium Fluoride-micronized | 5.00 |
| Saccharin 550 | 0.69 |
| Flavor agent (Raspberry 73562) | 0.64 |
| Colophonium-compendial grade | 32.31 |
| Mastic-compendial grade | 11.94 |
| Wax-containing shellac | 21.73 |
| White Beeswax USP | 0.49 |
| Totals | 100.0 |

The rheology properties of the Oral Care Composition 1 and Comparative Example 1 were measured. Table 3 shows the comparison of the rheology properties between Oral Care Composition 1 and Comparative Example 1.

TABLE 3

Rheology Comparison

| Comparison | Yield Strength (up) | Yield Strength (down) | High-Shear Viscosity |
|---|---|---|---|
| Comparative Example 1 | 15 Pa | 6.7 Pa | 0.4 Pa·s |
| Oral Care Composition 1 | 286 Pa | 184 Pa | 3.35 Pa·s |

As can be observed, the Oral Care Composition 1 of the present invention unexpectedly provided much higher yield strength (up), yield strength (down), and high-shear viscosity then the Comparative Example 1. This provides an optimal suspension system for film forming compositions. Further, the inventive Oral Care Composition 1 provided the ideal rheology properties to achieve an optimum active suspension of fluoride in a varnish formulation. Specifically, a high viscosity value is desirable for an improved active suspension and product stability in a non-aqueous system.

Finally, both Oral Care Compositon 1 and Comparative Example 1 were applied to a tooth surface and the color was observed, the Oral Care Composition 1 provided a translucent white film on the enamel surface when applied to teeth, whereas the Comparative Example 1 provided a yellowish finish on the enamel surface when applied to teeth.

Active Ingredient (Fluoride) Premix 2

An active ingredient (fluoride) premix was made by adding ethanol (50.00 wt %) and saccharin (0.67 wt %) to a plastic beaker and mixing until the saccharin was dissolved. The methacrylate copolymer, EUDRAGIT®, (12.50 wt %) was slowly added while mixing with an overhead mixer until dissolved. Sodium fluoride (4.97 wt %) was added and mixed for 30 minutes until a homogeneous solution was formed.

Ethylcellulose Premix 2

An ethylcellulose premix was made by slowly adding AQUALON® N22 ethylcellulose (5.00 wt %) to ethanol (19.22 wt %) in a plastic beaker, and slowly mixing to avoid lumps. Once the ethylcellulose was incorporated, fumed silica (6.00 wt %) was added and mixed for 30 minutes until the solution was homogenous.

Oral Care Composition 2

The active ingredient (fluoride) premix 2 and the ethylcellulose premix 2 were mixed together in a plastic beaker. CITROFLEX® A-4 (1.00 wt %) was added and mixed for 10 minutes. Raspberry 73562 (0.64 wt %) was added and mixed for 15 minutes to make Oral Care Composition 2. The specific gravity of the Oral Care Composition 2 was measured at 0.954.

TABLE 4

Example Oral Care Composition 2

| Ingredients | Weight % |
|---|---|
| Ethanol | 69.22 |
| Sodium Fluoride | 4.97 |
| Saccharin | 0.67 |
| Fumed Silica | 6.00 |
| Flavor agent (Raspberry 735621) | 0.64 |
| AQUALON ® N22 Ethylcellulose | 5.00 |
| CITROFLEX ® A-4 | 1.00 |
| EUDRAGIT ® | 12.50 |
| Totals | 100.00 |
| Specific Gravity | 0.954 |

As can be observed from the above examples, it has surprisingly been found that an oral care composition of the present invention has phase stability and imparts little color when applied to the teeth. Furthermore, it has been surprisingly discovered that the oral care composition also has good rheological and film-forming properties, and provides effective time-release of fluoride to the teeth. In addition, when applied to a tooth surface, the oral care composition dries out as a cosmetically desirable clear film.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility. It is therefore intended by the appended claims to cover any and all such applications, modifications and embodiments within the scope of the present invention.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. It should also be appreciated that the numerical limits may be the values from the examples. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

What is claimed is:

1. An oral care composition comprising:
   3 wt % to 7 wt % of ethylcellulose;
   15 wt % to 25 wt % hydrogenated rosin;
   0.1 wt % to 3 wt % acetyl tributyl citrate;
   1 wt % to 10 wt % sodium fluoride;
   50 wt % to 70 wt % solvent, wherein the solvent is ethanol; and
   1 wt % to 10 wt % fumed silica.

2. The oral care composition of claim 1, wherein the composition further comprises a methacrylate copolymer.

3. The oral care composition of claim 2, wherein the methacrylate copolymer is a copolymer of dimethylaminoethyl methacrylate, butyl methacrylate and methyl methacrylate.

4. The oral care composition of claim 1, wherein the fumed silica is present in an amount from 4 wt % to 6 wt %, based on the total weight of the composition.

5. The oral care composition of claim 1, wherein the oral care composition is nonaqueous.

6. The oral care composition of claim 1, wherein the oral composition is free of shellac and beeswax.

7. The oral care composition of claim 1, wherein the oral care composition has a yield stress (up) of 280 Pa to 290 Pa, a yield stress (down) of 180 Pa to 190 Pa, and a high-shear viscosity of 3.25 Pa·s to 3.45 Pa·s, at a temperature of 25° C.

8. The oral care composition of claim 4,
   wherein the composition comprises from 10 wt % to 15 wt % of methacrylate copolymer.

9. A method of making an oral care composition according to claim 1 comprising:
   mixing sodium fluoride, hydrogenated rosin, and ethanol to make an active ingredient premix; mixing ethylcellulose, ethanol, and fumed silica to make an ethylcellulose premix; and mixing the active ingredient premix, the ethylcellulose premix, and acetyl tributyl citrate to make the oral care composition.

10. The method of making an oral care composition of claim 9, wherein the hydrogenated rosin is present in an amount from 19 wt % to 21 wt %, based on the total weight of the composition.

11. The method of making an oral care composition of claim 9, wherein sodium fluoride is present in an amount from 4 wt % to 5 wt %, based on the total weight of the composition.

12. The method of making an oral care composition of claim 9, wherein the oral care composition is nonaqueous.

13. The method of making an oral care composition of claim 9, wherein the oral composition is free of shellac and beeswax.

14. The method of making an oral care composition of claim 9, wherein the oral care composition has a yield stress (up) of 280 Pa to 290 Pa, a yield stress (down) of 180 Pa to 190 Pa, and a high-shear viscosity of 3.25 Pa·s to 3.45 Pa·s, at a temperature of 25° C.

\* \* \* \* \*